US011812181B2

(12) United States Patent
Mitani

(10) Patent No.: US 11,812,181 B2
(45) Date of Patent: Nov. 7, 2023

(54) VIDEO ROUTING IN AN OPERATING THEATER

(71) Applicant: Sony Corporation, Tokyo (JP)

(72) Inventor: Tetsuya Mitani, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 46 days.

(21) Appl. No.: 17/259,946

(22) PCT Filed: Jul. 24, 2019

(86) PCT No.: PCT/EP2019/069947
§ 371 (c)(1),
(2) Date: Jan. 13, 2021

(87) PCT Pub. No.: WO2020/020958
PCT Pub. Date: Jan. 30, 2020

(65) Prior Publication Data
US 2021/0274103 A1 Sep. 2, 2021

(30) Foreign Application Priority Data

Jul. 24, 2018 (EP) .................... 18185367

(51) Int. Cl.
*H04N 5/268* (2006.01)
*H04N 5/262* (2006.01)
(Continued)

(52) U.S. Cl.
CPC ............ *H04N 5/268* (2013.01); *A61B 90/37* (2016.02); *G06F 3/0482* (2013.01);
(Continued)

(58) Field of Classification Search
CPC ...... H04N 5/268; H04N 5/247; H04N 5/2628; H04N 2005/2255; A61B 90/37;
(Continued)

(56) References Cited

U.S. PATENT DOCUMENTS

| 2008/0159653 | A1 | 7/2008 | Dunki-Jacobs et al. |
| 2013/0030285 | A1* | 1/2013 | Vaillant ............... A61B 6/5235 600/427 |

(Continued)

FOREIGN PATENT DOCUMENTS

| JP | 2015-083082 A | 4/2015 |
| WO | 2016/072059 A1 | 5/2016 |
| WO | 2017/089910 A1 | 6/2017 |

OTHER PUBLICATIONS

International Search Report and Written Opinion dated Dec. 16, 2019, received for PCT Application No. PCT/EP2019/069947, filed on Jul. 24, 2019, 13 pages.

(Continued)

*Primary Examiner* — Alazar Tilahun
(74) *Attorney, Agent, or Firm* — XSENSUS LLP

(57) ABSTRACT

An audiovisual controller for routing input/output imaging data in an operating theater is disclosed. The controller comprises an imaging data input port for receiving surgical imaging data from an imaging data capturing device and an imaging data output port for transmitting said surgical imaging data to an output monitor for displaying the surgical imaging data. The controller is configured for receiving orientation information regarding the orientation of the imaging data capturing device and the output monitor. The controller is configured for adjusting an orientation or position of the displayed surgical imaging data as function of the orientation information.

14 Claims, 6 Drawing Sheets

(51) Int. Cl.
  *G06F 3/0482* (2013.01)
  *G06F 3/0484* (2022.01)
  *A61B 90/00* (2016.01)
  *G16H 40/67* (2018.01)
  *G16H 40/20* (2018.01)
  *G16H 30/20* (2018.01)
  *H04N 23/90* (2023.01)
  *H04N 23/50* (2023.01)

(52) U.S. Cl.
  CPC ............ *G06F 3/0484* (2013.01); *G16H 30/20* (2018.01); *G16H 40/20* (2018.01); *G16H 40/67* (2018.01); *H04N 5/2628* (2013.01); *H04N 23/90* (2023.01); *H04N 23/555* (2023.01)

(58) Field of Classification Search
  CPC ............ A61B 1/00004; A61B 1/00011; A61B 1/00045; A61B 34/25; G06F 3/0482; G06F 3/0484; G16H 30/20; G16H 40/20; G16H 40/67; G16H 20/40
  See application file for complete search history.

(56) References Cited

U.S. PATENT DOCUMENTS

| | | | |
|---|---|---|---|
| 2015/0018622 A1* | 1/2015 | Tesar | A61B 90/20 600/202 |
| 2016/0316259 A1* | 10/2016 | Kambhatla | H04N 21/44227 |
| 2018/0098049 A1* | 4/2018 | Sugano | A61B 34/25 |

OTHER PUBLICATIONS

Office Action dated Jul. 4, 2023, in corresponding Japanese patent Application No. 2021-503731, 10 pages.

* cited by examiner

Monitor detection

Table1

| Connector Info | Coordinate on UI |
|---|---|
| Switch1/Port1 | X=10, y=20 |
| Switch1/Port2 | X=100, y=70 |

Table2

| IPC ID | Connector Info | Icon image |
|---|---|---|
| 1 | Switch1/Port1 | Image1 |
| 2 | Switch1/Port2 | image2 |

FIG. 7

1: First, according the position of network connector in actual operation room, setup connector location data. (like table1)

2: When IPC is connected to the network, IPC send announce message include unique id and network connector info to server. As a result, server can hold information like this table2.

3: The server can refer to the IPC connector info and display this IPC icon in the corresponding coordinates on the UI.
The server can also hold icon images of each IPC. In this case, the user can set a suitable image. (For example, actual photos etc.)

FIG. 8

VIDEO ROUTING IN AN OPERATING THEATER

CROSS-REFERENCE TO RELATED APPLICATIONS

The present application is based on PCT filing PCT/EP2019/069947, filed Jul. 24, 2019, which claims priority to EP 18185367.2, filed Jul. 24, 2018, the entire contents of each are incorporated herein by reference.

TECHNICAL FIELD OF THE INVENTION

The present invention relates to the field of image displaying and control thereof. More specifically, it relates to a controller and corresponding user interface for managing, controlling and/or visualizing displaying of imaging data, e.g. video data, in an operating theater.

BACKGROUND OF THE INVENTION

In an operating theater, there are many video capturing devices and many video display devices. Therefore it is necessary to centrally manage with an audiovisual routing controller such video capturing device and video display devices. In a typical user interface of such a controller, icons representing each video capturing device and each video display device are present. In order to perform video routing, the user needs to know which icon represents which device. For the video capturing devices, for example a thumbnail image of the video output can be displayed on the user interface.

On the other hand, video display devices often are difficult to distinguish. Monitors often have a same similar appearance. Sometimes also the same video data is displayed on multiple displays, so that the monitors cannot be uniquely identified based on the video data that is display. Furthermore, mobile cart monitors may be used, so there is a possibility that the placement of these device will be changed, e.g. per kind of operations or per user.

SUMMARY OF THE INVENTION

It is an object of embodiments of the present invention to provide good controllers and user interfaces for use in an operating theater.

It is an advantage of embodiments of the present invention that controllers, user interfaces and corresponding operating theaters are provided allowing efficient identification of IPC, e.g. video output devices, for example for efficient performing of video routing.

It is an advantage of embodiments of the present invention that controllers, user interfaces and corresponding operating theaters are provided allowing efficient use of the image data, e.g. video data, displayed.

The present invention relates to an audiovisual controller for routing input/output imaging data in an operating theater, the controller being configured for receiving orientation information regarding the orientation of at least one imaging data capturing device and of at least one output monitor and the controller being configured for adjusting an orientation or position of the displayed surgical imaging data as function of the orientation information. It is an advantage of embodiments of the present invention that the displayed surgical imaging data can be displayed in a manner that is user-friendly. It is an advantage of embodiments of the present invention that the displayed surgical imaging data can be displayed in a manner that avoids erroneous interpretation.

The controller may be configured for receiving position information regarding of at least one imaging data capturing device and of at least one output monitor, and the controller being configured for adjusting the orientation and the position of the displayed surgical imaging data as function of the orientation information and the position information.

The controller may comprise automated adjustment of the orientation or position of the displayed surgical imaging data as function of the orientation information. It is an advantage of embodiments of the present invention that adjustment can be performed in an automated way, allowing the medical staff to focus on the surgical intervention rather than how the images are displayed.

Adjusting an orientation or position of the displayed surgical imaging data may comprise adjusting an orientation or position of the displayed surgical imaging data when the orientation of the imaging data capturing device and the output monitor is outside a predetermined range.

Adjusting an orientation or position of the displayed surgical imaging data as function of the orientation information may comprise flipping or rotating the displayed surgical imaging data.

The controller may be configured for obtaining a new selection of an imaging data capturing device and of at least one output monitor on which the imaging data of the imaging data capturing device is to be displayed, and for adjusting the network configuration for outputting the imaging data on said at least one output monitor. The controller typically is programmed for configuring and where necessary reconfiguring the routing for the imaging data so that the proper imaging data is routed to the proper output monitor. According to embodiments of the present invention, this is also done with an adapted position and orientation, where necessary.

The controller may be adapted for controlling a plurality of monitors in an operating theater and wherein the audiovisual controller provides a user interface for displaying a layout of the operating theater indicating at least orientations or positions of the plurality of monitors and the controller, based on positional information received from the monitors. It is an advantage of embodiments of the present invention that an improved overview of the typically numerous monitors is obtained.

The positional information may be determined based on network connection information from the monitors.

The layout may be automatically updated using an updated of the network connection information from a monitor, when a position of the monitor changes.

The user interface may be adapted for displaying an overview comprising a representation regarding the different monitors or their position on the one hand and information regarding the monitors' connection in a network in the operating theater. It is an advantage of embodiments of the present invention that different monitors are easily distinguishable. The latter is advantageous, especially since monitors often have a similar appearance. It is an advantage of embodiments of the present invention that the position of monitors in the operating theater can be easily identified. The latter is especially useful since mobile cart monitors may be used, so there is a possibility that the placement of the devices are changed, e.g. depending on the surgery performed.

The user interface may be furthermore adapted for displaying an overview comprising a representation regarding the different monitors or their position on the one hand and the image data displayed on the respective monitors.

The representation regarding the different monitors or their position in the overview and an image displayed on the different monitors may be shown with a common visual element. It is an advantage of embodiments of the present invention that it is easy to recognize which monitor is represented on the controller.

The common visual element may be an indication in the same colour. It is an advantage of embodiments of the present invention that the monitor may be identified by showing a coloured frame or mark on the image displayed on the monitor, the coloured frame or mark being of the same colour as the representation shown in the overview.

The controller may be programmed for, upon selection of a monitor in the overview by a user, identifying the monitor by an indication on that monitor. The indication on that monitor may be the common visual element as discussed earlier, the common visual element typically being shown on the image data displayed on the monitor, or may be any other auditive or visual indication, such as or example a sound signal, a temporarily change in the display of the image data by e.g. a variation in intensity, a control lamp being activated, etc. Such indication on the monitor may be disabled if the user does not require it anymore.

The controller may be adapted for, upon activating a new monitor in the network, adding the new monitor to the overview.

The present invention also relates to an operating theater comprising an audiovisual controller as described above.

The present invention furthermore relates to an audiovisual controller for routing input/output imaging data in an operating theater, the controller being adapted for controlling a plurality of monitors in an operating theater, wherein the audiovisual controller provides a user interface for displaying a layout of the operating theater indicating at least positions of the plurality of monitors and the controller, based on positional information received from the monitors. It is an advantage of embodiments of the present invention that an improved overview of the typically numerous monitors is obtained.

The positional information may be determined based on network connection information from the monitors.

The layout may be automatically updated using an updated of the network connection information from a monitor, when a position of the monitor changes.

The user interface may be adapted for displaying an overview comprising a representation regarding the different monitors or their position on the one hand and information regarding the monitors' connection in a network in the operating theater. It is an advantage of embodiments of the present invention that different monitors are easily distinguishable. The latter is advantageous, especially since monitors often have a similar appearance. It is an advantage of embodiments of the present invention that the position of monitors in the operating theater can be easily identified. The latter is especially useful since mobile cart monitors may be used, so there is a possibility that the placement of the devices are changed, e.g. depending on the surgery performed.

The user interface may be furthermore adapted for displaying an overview comprising a representation regarding the different monitors or their position on the one hand and the image data displayed on the respective monitors.

The representation regarding the different monitors or their position in the overview and an image displayed on the different monitors may be shown with a common visual element. It is an advantage of embodiments of the present invention that it is easy to recognize which monitor is represented on the controller.

The common visual element may be an indication in the same colour. It is an advantage of embodiments of the present invention that the monitor may be identified by showing a coloured frame or mark on the image displayed on the monitor, the coloured frame or mark being of the same colour as the representation shown in the overview.

The controller may be programmed for, upon selection of a monitor in the overview on the user interface by a user, identifying the monitor by an indication on that monitor.

The indication on that monitor may be the common visual element as discussed earlier, the common visual element typically being shown on the image data displayed on the monitor, or may be any other auditive or visual indication, such as or example a sound signal, a temporarily change in the display of the image data by e.g. a variation in intensity, a control lamp being activated, etc. Such indication on the monitor may be disabled if the user does not require it anymore.

The controller may be configured for obtaining a new selection of an imaging data capturing device and of at least one output monitor on which the imaging data of the imaging data capturing device is to be displayed, and for adjusting the network configuration for outputting the imaging data on said at least one output monitor. The controller typically is programmed for configuring and where necessary reconfiguring the routing for the imaging data so that the proper imaging data is routed to the proper output monitor. According to embodiments of the present invention, this is also done with an adjusted position or orientation where required.

The present invention also relates to an operating theater comprising an audiovisual controller as described above.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

BRIEF DESCRIPTION OF THE DRAWINGS

FIG. 7 is a schematic overview of information that can be stored, when implementing an embodiment of the present invention.

FIG. 8 is an exemplary method as can be used for generating a layout of monitors in an operating theater according to an embodiment of the present invention.

Figure 1:
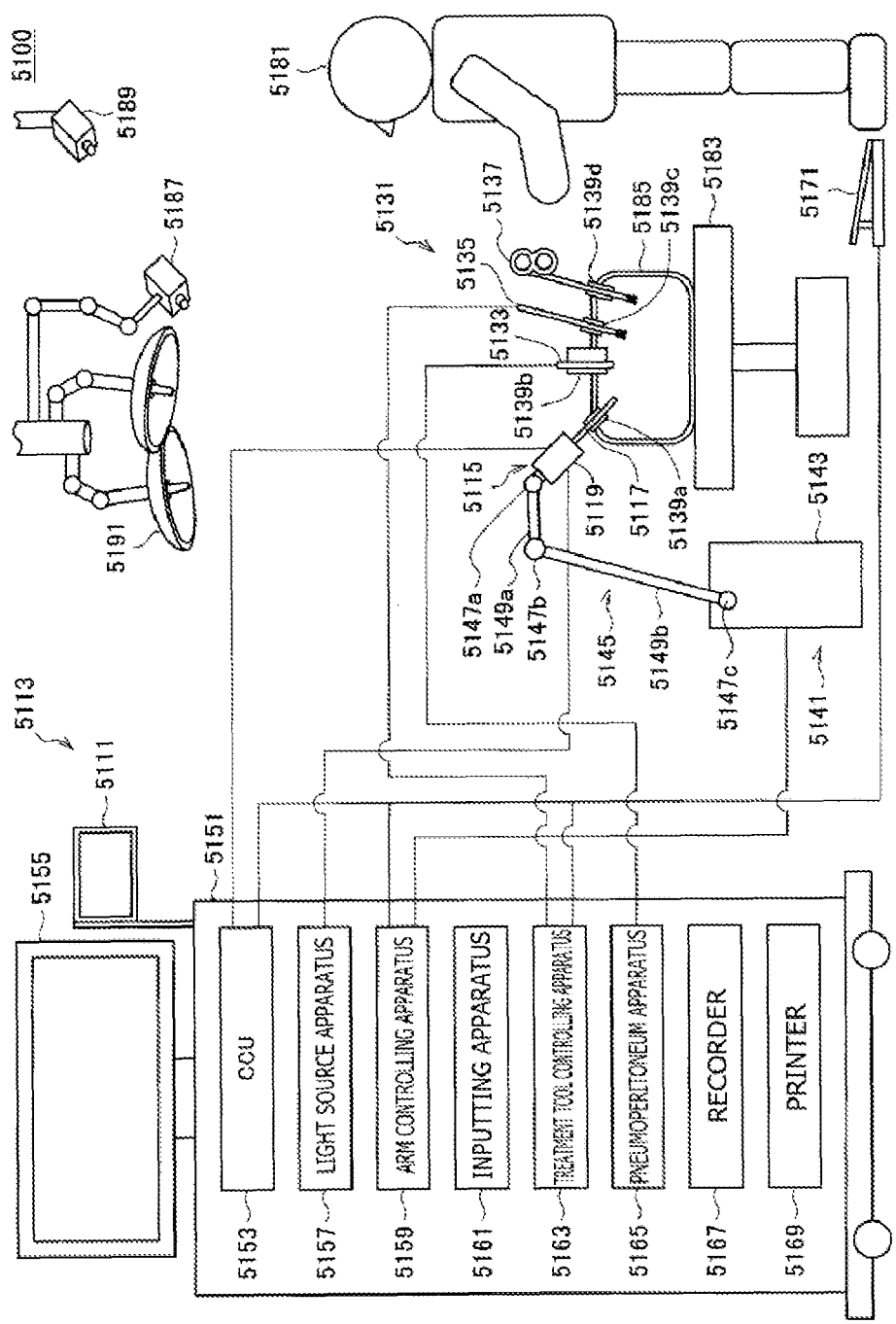
FIG. 1 illustrates an exemplary of an operating theater, wherein embodiments of the present invention can be implemented.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein. Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

By way of illustration, the context for which the image processing according to embodiments of the present invention are described, will be illustrated by the description of an exemplary operating theater and imaging system (in the present example an endoscopic system). It will be clear that this is only given by way of illustrating the context of embodiments of the present invention, but that these embodiments are also applicable to other types of operating theaters and to other types of imaging systems. FIG. 1 is a view illustrating an example of a state of surgery applied to a surgery room system according to the prior art. A ceiling camera 5187 and a surgery field camera 5189 are provided on the ceiling of the surgery room such that it can image the hands of a surgeon (medical doctor) 5181 who performs treatment for an affected area of a patient 5185 on a patient bed 5183 and the entire surgery room. The ceiling camera 5187 and the surgery field camera 5189 may include adjustment functions (magnification, focal distance, and so forth). An illumination 5191 is provided on the ceiling of the surgery room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 can be connected for cooperation with each other, e.g. through an audiovisual controller and a surgery room controlling apparatus. A centralized operation panel 5111 can provided in the surgery room, and the user can suitably operate the apparatus existing in the surgery room through the centralized operation panel 5111.

Still referring to FIG. 1, a configuration of an endoscopic surgery system 5113 is described in detail. It includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139*a* to 5139*d* can be used to puncture the abdominal wall. Then, a lens barrel 5117 of the endoscope 5115 and the other surgical tools 5131 are inserted into body lumens of the patient 5185 through the trocars 5139*a* to 5139*d*. In the example depicted, as the other surgical tools 5131, a pneumoperitoneum tube 5133, an energy treatment tool 5135 (for performing incision, peeling, sealing vessels or the like by high frequency current or ultrasonic vibration) and forceps 5137 are inserted into body lumens of the patient 5185. However, the surgical tools 5131 depicted are mere examples. Various surgical tools which are generally used in endoscopic surgery such as, for example, a pair of tweezers or a retractor may be used.

An image of a surgical region in a body lumen of the patient 5185 picked up by the endoscope 5115 can be displayed on one or more display apparatus 5155. A pneumoperitoneum apparatus 5165 can be used to feed gas into a body lumen of the patient 5185 through the pneumoperitoneum tube 5133 to inflate the body lumen in order to secure the field of view of the endoscope 5115 and secure the working space for the surgeon. The surgeon 5181 can use the energy treatment tool 5135 or the forceps 5137 while watching the image of the surgical region displayed on the display apparatus 5155 to perform such treatment as, for example, resection of an affected area.

The endoscope 5115 may include a lens barrel 5117 which has a region of a predetermined length from a distal end thereof to be inserted into a body lumen of the patient 5185, and a camera head 5119 connected to a proximal end of the lens barrel 5117. The endoscope 5115 of FIG. 1 is depicted as a hard mirror having the lens barrel 5117 of the hard type, but the endoscope 5115 may otherwise be configured as a soft mirror having the lens barrel 5117 of the soft type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body lumen of the patient 5185 through the objective lens. The endoscope 5115 may be a direct view mirror or may be a perspective view mirror or a side view mirror.

(Camera Head and CCU)

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal can be transmitted as RAW data to a camera control unit (CCU) 5153. The camera head 5119 may have a function incorporated therein for suitably driving the optical system of the camera head 5119 to adjust the magnification and the focal distance.

The CCU 5153 may include a central processing unit (CPU), a graphics processing unit (GPU) or the like and may integrally control operation of the endoscope 5115 and/or the display apparatus 5155. For example the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. The CCU 5153 may be connected to an audiovisual controller and provide the image signal for which the image processes have been performed.

Further, the CCU 5153 may include a communication unit for transmitting a control signal to the camera head 5119 to control driving of the camera head 5119. The control signal may include information relating to an image pickup condition such as information that a frame rate of a picked up image is designated, information that an exposure value upon image picking up is designated and/or information that a magnification and a focal point of a picked up image are designated. Further, the camera head 5119 may include a communication unit for receiving a control signal for controlling driving of the camera head 5119 from the CCU 5153. The communication unit provides the received control signal to a camera head controlling unit 5129.

It is to be noted that the image pickup conditions such as the frame rate, exposure value, magnification or focal point can be set automatically by the CCU 5153 (e.g. by a control unit 5177 thereof) on the basis of an acquired image signal. In other words, an auto exposure (AE) function, an auto focus (AF) function and an auto white balance (AWB) function can be incorporated in the endoscope 5115. Aside from the endoscope also other types of imaging may be applied. Typically in the operating theater, a plurality of image data capturing devices and a plurality of image displaying devices will be present. These typically will be managed centrally in an audiovisual routing controller. In a typical user interface of such a controller, icons representing each video capturing device and each video display device are present. In order to perform video routing, the user needs to know which icon represents which device. Furthermore, also the relative relation between video capturing devices and video displaying devices is important, as it may affect the appropriate use of the image data, e.g. video data, by the medical staff.

In a first aspect, the present invention relates to an audiovisual controller for routing input/output imaging data in an operating theater. As indicated above, typically a plurality of imaging capturing devices and imaging displaying devices, such as for example video capturing devices and video displaying devices such as monitors are present. The controller typically allows controlling of the routing of the image data captured so that the image data, e.g. video data, can be displayed at an appropriate monitor. In some embodiments, the controller may comprise an imaging data input port for receiving surgical imaging data from an imaging data capturing device so that the data can be displayed on a user interface of the controller. According to embodiments of the present invention, the controller is configured for receiving orientation information regarding the orientation of at least one imaging data capturing device and of at least one output monitor and the controller is being configured for adjusting an orientation or position of the displayed surgical imaging data as function of the orientation information. Displaying with a proper orientation may provide a more user-friendly system. The displayed surgical imaging data can, using the controller, be displayed in a manner that avoids erroneous interpretation. The adjustment may be automated adjustment of the orientation or position of the displayed surgical imaging data as function of the orientation information. Adjusting an orientation or position of the displayed surgical imaging data may in some embodiments comprise adjusting an orientation or position of the displayed surgical imaging data when the orientation of the imaging data capturing device and the output monitor is outside a predetermined range. Adjusting an orientation or position of the displayed surgical imaging data as function of the orientation information may comprise flipping or rotating the displayed surgical imaging data.

The audiovisual controller typically may perform the function of routing the imaging information to be displayed on a given monitor to that output monitor. When a new imaging combination of imaging data and output monitor on which it is to be displayed is announced, the controller adjusts the network configuration for outputting the imaging data on said at least one output monitor. It is in some embodiments programmed for configuring and where necessary reconfiguring the routing for the imaging data so that the proper imaging data is routed to the proper output monitor.

The audiovisual controller also may provide additional functionalities, e.g. a functionality for easily identifying a monitor and/or a functionality for displaying a layout of the different monitors in the operating theater. These ideas may be combined in the audiovisual controller, but embodiments of the present invention also relate to audiovisual controllers providing only this functionality of this functionality with other functionalities, and not necessarily with the functionality of orienting the displayed image as function of an orientation relationship between the image capturing device and the image displaying device.

The audiovisual controller thus may in some embodiments be adapted for controlling a plurality of monitors in an operating theater. It may provide a user interface for displaying a layout of the operating theater indicating at least positions of the plurality of monitors and the controller, based on positional information received from the monitors. The latter results in an improved overview of the typically numerous monitors is obtained. The positional information may be determined based on network connection information from the monitors. The layout may be automatically updated using an updated of the network connection information from a monitor, when a position of the monitor changes. In some embodiments, the user interface is adapted for displaying an overview comprising a representation regarding the different monitors or their position on the one hand and information regarding the monitors' connection in a network in the operating theater. It is an advantage of embodiments of the present invention that different monitors are easily distinguishable. The latter is advantageous, especially since monitors often have a similar appearance.

The user interface may furthermore be adapted for displaying an overview comprising a representation regarding the different monitors or their position on the one hand and the image data displayed on the respective monitors. This may be performed by showing the icons on the user interface and the displayed data with a common visual element, e.g. an indication in the same colour.

The controller may also be programmed for, upon selection of a monitor in the overview by a user, identifying the monitor by an indication on that monitor. It may be adapted for, upon activating a new monitor in the network, adding the new monitor to the overview. Further features may be as those shown in the examples.

In one aspect, the present invention also relates to a user interface corresponding with the controller as indicated above.

The present invention in one aspect also relates to an operating theater comprising an audiovisual controller as described above.

Figure 2:
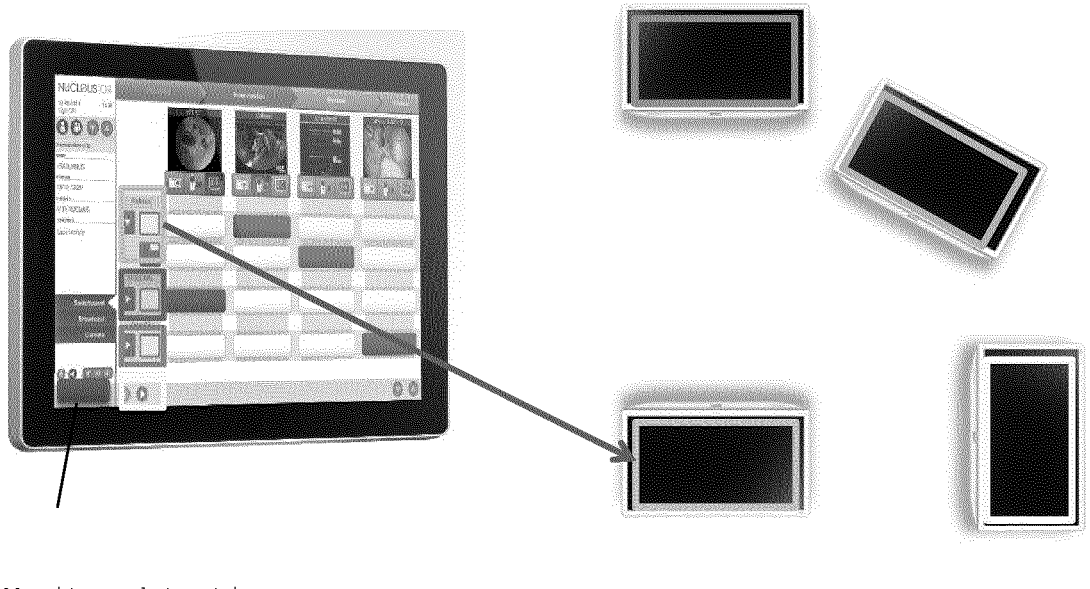
FIG. 2 is an example of a user interface allowing easy detection of a monitor, according to an embodiment of the present invention.
Figure 3:
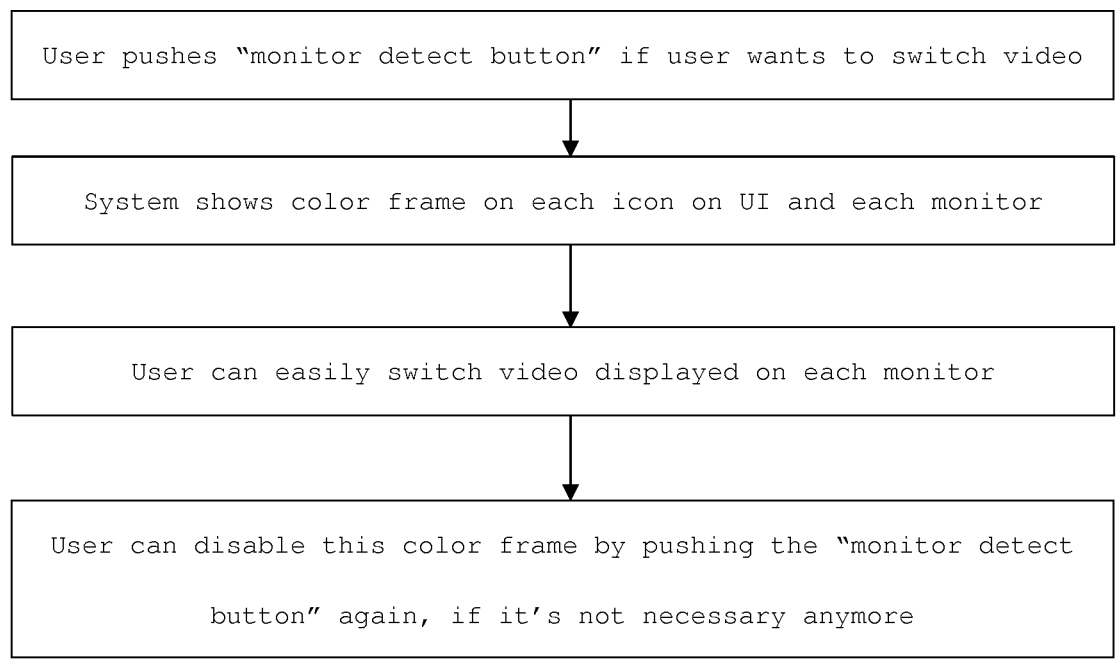
FIG. 3 is an example of method steps that are applied for easy detection of a monitor, according to an embodiment of the present invention.

By way of illustration, embodiments of the present invention not being limited thereto, some examples are shown below, illustrating standard and optional features of embodiments of the present invention. In a first example, an illustration is given of a user interface allowing easy detection of a monitor in an operating theater. The latter is especially suitable in case a lot of monitors are present in the operating room. In the present example, color matching between the icons on the user interface and the actual monitors is used. FIG. 2 illustrates an example of the user interface and the fact how color matching is used. In FIG. 3, a possible procedure is shown. In a first step, the user pushes the "monitor detect button", if the user wants to switch video. In a second step, following the activation of the monitor detect button, the system shows a color frame or some color mark on each of the icons on the User Interface and on each of the monitors. The user can thus, in a third step, easily switch video displayed on each of the monitors, as the monitors are easily identifiable. The user can disable the color frame on the monitors, e.g. in some embodiments by pushing the monitor detect button again, if the user does not need the easy identification anymore. The user interface may be especially suitable for cases where a user connect mobile cart monitor is used, since the user interface may be configure for automatically showing the monitor when it is included in the network.

Figure 4:
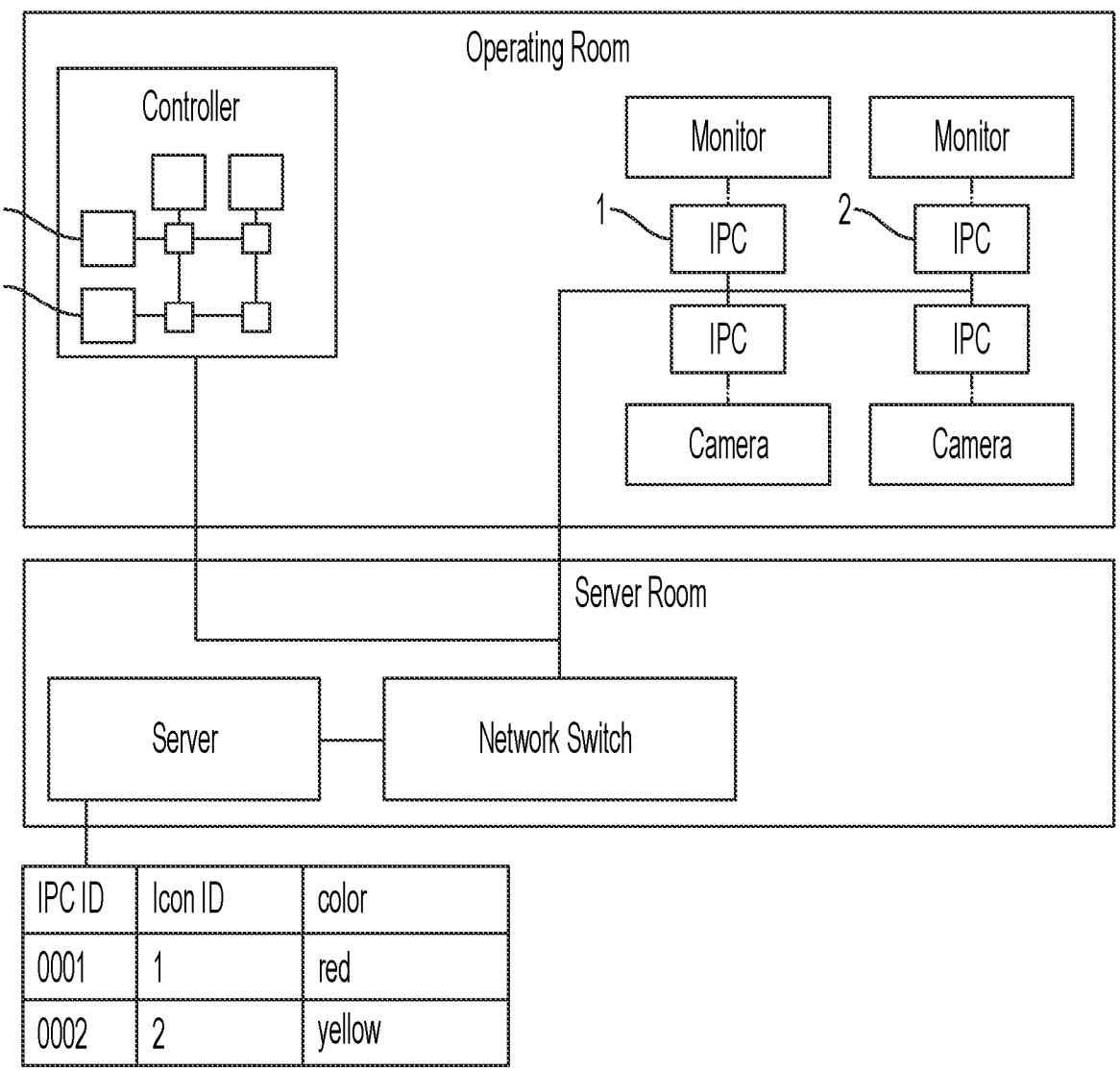
FIG. 4 is an example of a configuration that can be used in an embodiment of the present invention.
Figure 5:
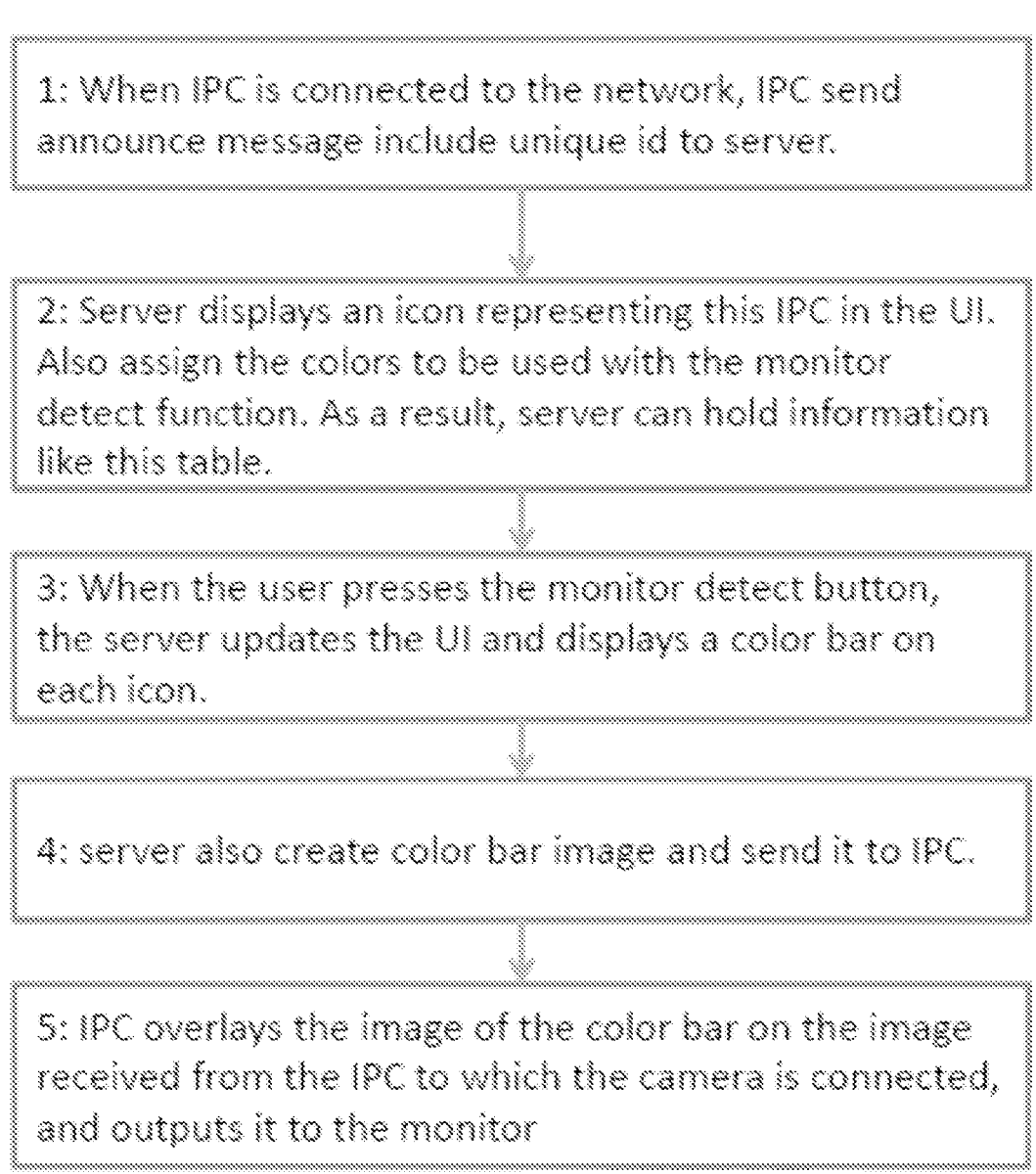
FIG. 5 is an example of a method for identifying a monitor, as can be used in an embodiment of the present invention.

The underlying process is shown in FIG. 4 and FIG. 5. In FIG. 4 a schematic representation is shown of the configuration. The controller with the user interface is shown indicating the different IPC's, in the present example being monitors on the one hand and on the other hand video capturing means. The different IPC components are interconnected through a network which typically is controlled via a network switch. The network switch typically may be positioned outside the operating theater, i.e. in a server room, together with the server. The server typically is adapted for linking the different monitors with a specific visual element, e.g. a specific color dedicated for each monitor allowing to easily link the icons on the user interface and the monitors by using a common visual element (e.g. color).

In FIG. 5, an example of an underlying process that can be used also is illustrated. In a first step, when an IPC, e.g. from a monitor, is connected to the network, the IPC sends an announce message including a unique ID to the server. In a second step, the server displays an icon representing this IPC in the user interface. Also a color is assigned to be used with the monitor detect function. As a result, the server can hold this information, e.g. in a table. When the user then presses the monitor detect button, the server updates the user interface and displays a color bar on each icon. The server also creates a color bar image and sends it to the IPC, so it can be displayed on the monitor. The latter can e.g. be performed by overlaying the image of the color bar on the image received from the IPC to which the camera is connected and outputs it to the monitor.

Figure 6:
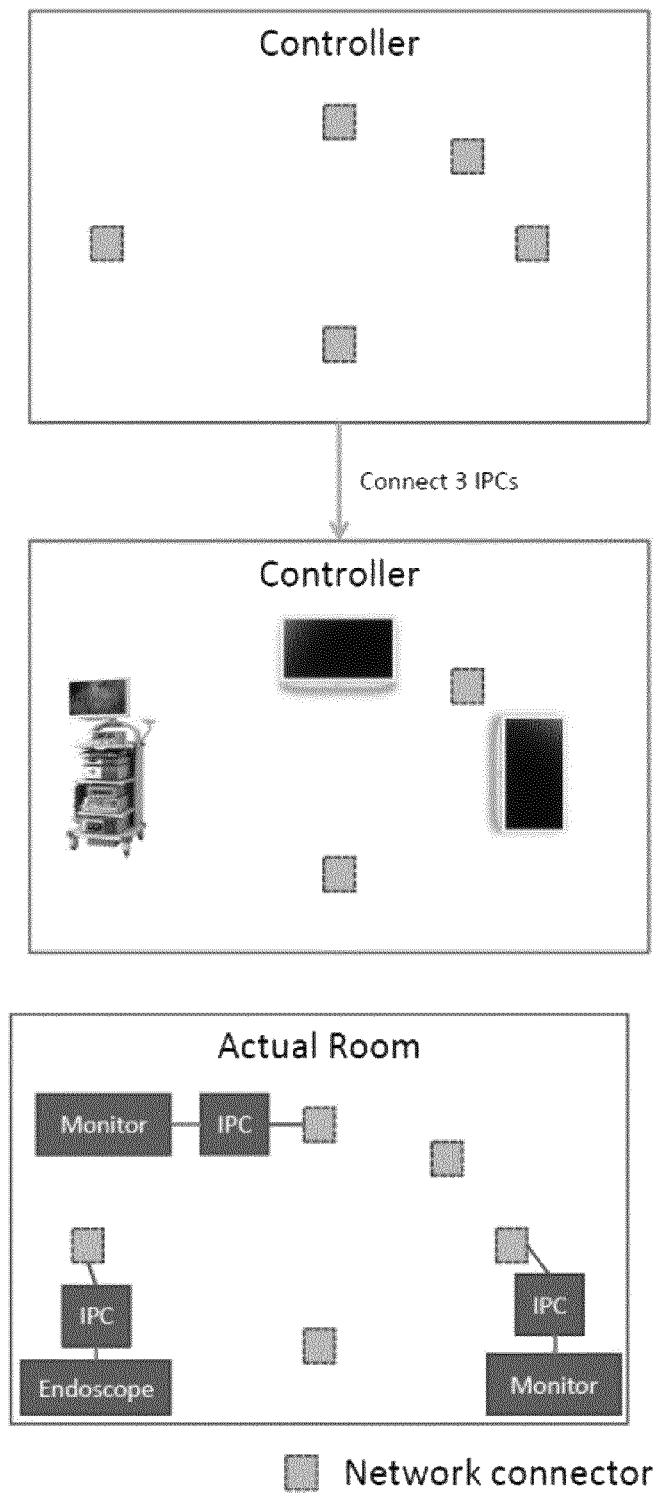
FIG. 6 is a schematic overview of a user interface illustrating a layout of monitors in an operating theater according to an embodiment of the present invention.

In a second example, a user interface is illustrated that provides a layout of different IPC components corresponding monitors, in an operating theater. FIG. 6 illustrates a layout of an operating theater wherein three monitors are connected to the network. In the middle image, a representation of the monitors that are connected is shown, and their relative position is indicated. In the bottom illustration the connection of the three components via their network connector is indicated. FIG. 7 illustrates two tables of information that can be captured and listed.

FIG. 8 illustrates an example of a possible underlying process. In a first step, according to the position of the network connector in the actual operating theater, the connector location data is setup, as for example shown in table 1 of FIG. 7. When an IPC is connected to the network, in a second step, the IPC sends an announce message including a unique ID and network connector info to the server. As a result, the server can hold this information, as shown in table 2 of FIG. 7. In a third step, the server can refer to the IPC connector info and display an IPC icon at the corresponding coordinates in the user interface. The server can also hold icon images of each IPC. In this case, the user can even set a suitable image, such as for example an actual photo.

The following numbered paragraphs provide further example aspects and features of the present technique:

Paragraph 1. An audiovisual controller for routing input/output imaging data in an operating theater, the controller being configured for receiving orientation information regarding the orientation of at least one imaging data capturing device and of at least one output monitor and the controller being configured for adjusting an orientation or position of the displayed surgical imaging data as function of the orientation information.

Paragraph 2. An audiovisual controller according to paragraph 1, the controller being configured for receiving position information regarding at least one imaging data capturing device and of at least one output monitor, and the controller being configured for adjusting the orientation and the position of the displayed surgical imaging data as function of the orientation information and the position information.

Paragraph 3. An audiovisual controller according to paragraph 1, wherein the controller comprises automated adjustment of the orientation or position of the displayed surgical imaging data as function of the orientation information.

Paragraph 4. An audiovisual controller according to any of the previous paragraphs, wherein adjusting an orientation or position of the displayed surgical imaging data comprises adjusting an orientation or position of the displayed surgical imaging data when the orientation of the imaging data capturing device and the output monitor is outside a predetermined range.

Paragraph 5. An audiovisual controller according to any of the previous paragraphs, wherein adjusting an orientation or position of the displayed surgical imaging data as function of the orientation information comprises flipping or rotating the displayed surgical imaging data.

Paragraph 6. An audiovisual controller according to any of the previous paragraphs, wherein the controller is configured for obtaining a new selection of an imaging data capturing device and of at least one output monitor on which the imaging data of the imaging data capturing device is to be displayed, and for adjusting the network configuration for outputting the imaging data on said at least one output monitor.

Paragraph 7. An audiovisual controller according to any of the previous paragraphs, wherein the audiovisual controller is adapted for controlling a plurality of monitors in an operating theater and wherein the audiovisual controller provides a user interface for displaying a layout of the operating theater indicating at least orientations or positions of the plurality of monitors and the controller, based on positional information received from the monitors.

Paragraph 8. An audiovisual controller according to paragraph 7, wherein the positional information is determined based on network connection information from the monitors.

Paragraph 9. An audiovisual controller according to paragraph 8, wherein the layout is automatically updated using an updated of the network connection information from a monitor, when a position of the monitor changes.

Paragraph 10. An audiovisual controller according to any of paragraphs 7 to 9, wherein the user interface is adapted for displaying an overview comprising a representation regarding the different monitors or their position on the one hand and information regarding the monitors' connection in a network in the operating theater.

Paragraph 11. An audiovisual controller according to paragraph 10, wherein the user interface is furthermore adapted for displaying an overview comprising a representation regarding the different monitors or their position on the one hand and the image data displayed on the respective monitors.

Paragraph 12. An audiovisual controller according to any of paragraphs 10 or 11, wherein the representation regarding the different monitors or their position in the overview and an image displayed on the different monitors is shown with a common visual element.

Paragraph 13. An audiovisual controller according to paragraph 12, wherein the common visual element is an indication in the same colour.

Paragraph 14. An audiovisual controller according to any of paragraphs 12 or 13, wherein the controller is programmed for, upon selection of a monitor in the overview by a user, identifying the monitor by an indication on that monitor.

Paragraph 15. An audiovisual controller according to any of paragraphs 10 to 14, wherein the controller is adapted for, upon activating a new monitor in the network, adding the new monitor to the overview.

Paragraph 16. An operating theater comprising an audiovisual controller according to any of paragraphs 1 to 15.

Paragraph 17. An audiovisual controller for routing input/output imaging data in an operating theater, the controller being adapted for controlling a plurality of monitors in an operating theater, wherein the audiovisual controller provides a user interface for displaying a layout of the operating theater indicating at least positions of the plurality of monitors and the controller, based on positional information received from the monitors.

Paragraph 18. An audiovisual controller according to paragraph 17, wherein the positional information is determined based on network connection information from the monitors.

Paragraph 19. An audiovisual controller according to paragraph 18, wherein the layout is automatically updated using an updated of the network connection information from a monitor, when a position of the monitor changes.

Paragraph 20. An audiovisual controller according to any of paragraphs 17 to 19, wherein the user interface is adapted for displaying an overview comprising a representation regarding the different monitors or their position on the one hand and information regarding the monitors' connection in a network in the operating theater.

Paragraph 21. An audiovisual controller according to paragraph 20, wherein the user interface is furthermore adapted for displaying an overview comprising a representation regarding the different monitors or their position on the one hand and the image data displayed on the respective monitors.

Paragraph 22. An audiovisual controller according to any of paragraphs 20 or 21, wherein the representation regarding the different monitors or their position in the overview and an image displayed on the different monitors is shown with a common visual element.

Paragraph 23. An audiovisual controller according to paragraph 22, wherein the common visual element is an indication in the same colour.

Paragraph 24. An operating theater according to any of paragraphs 22 or 23, wherein the controller is programmed for, upon selection of a monitor in the overview on the user interface by a user, identifying the monitor by an indication on that monitor.

Paragraph 25. An operating theater comprising an audiovisual controller according to any of paragraphs 17 to 24.

The invention claimed is:

1. An audiovisual controller for routing input/output imaging data in an operating theater, the controller being configured to:
   route image data from a plurality of imaging data capturing devices;
   receive orientation information regarding an orientation from each of the imaging data capturing devices of the plurality of imaging data capturing devices;
   receive orientation information regarding an orientation at least one output monitor;
   receive position information regarding a position of each of the imaging data capturing devices of the plurality of imaging data capturing devices;
   receive position information regarding a position of each of the imaging data capturing devices and the at least output monitor; and
   automatically adjust an orientation and position of the imaging data to be displayed on the at least one output monitor in accordance with the orientation information of an imaging data capturing device of the plurality of imaging data capturing devices outputting image data to be displayed on the at least one output monitor and the orientation information of the at least one output monitor and the position information of the imaging data capturing device of the plurality of imaging data capturing devices to be displayed on the at least one output monitor and the position information of the at least one output monitor.

2. An audiovisual controller according to claim 1, wherein the controller is configured to:
   adjust an orientation or position of the displayed imaging data comprises adjusting an orientation or position of the displayed imaging data when the orientation of the imaging data capturing device of the plurality of imaging data capturing devices outputting image data to be displayed on the at least one output monitor and the orientation of the at least one output monitor is outside a predetermined range.

3. An audiovisual controller according to claim 1, wherein the controller is configured to:
   adjust an orientation or position of the displayed imaging data as function of the orientation information comprises flipping or rotating the displayed imaging data.

4. An audiovisual controller according to claim 1, wherein the controller is configured to obtain a new selection of an imaging data capturing device and of at least one output monitor on which the imaging data of the imaging data capturing device is to be displayed, and to adjust the network configuration for outputting the imaging data on said at least one output monitor.

5. An audiovisual controller according to claim 1, wherein the controller is configured to control a plurality of monitors in an operating theater and to provide a user interface for displaying a layout of the operating theater indicating at least orientations or positions of the plurality of monitors and the controller, based on positional information received from each of the plurality of monitors.

6. An audiovisual controller according to claim 5, wherein the controller is configured to determine positional information based on network connection information from each of the plurality of monitors.

7. An audiovisual controller according to claim 6, wherein the controller is configured to automatically updated the layout using an updated of the network connection information from a monitor of the plurality of monitors, when a position of the monitor changes.

8. An audiovisual controller according to claim 5, wherein the user interface is adapted for displaying an overview comprising a representation regarding each of the plurality of monitors at their relative position and information regarding each of the plurality of monitors' connection in a network in the operating theater.

9. An audiovisual controller according to claim 8, wherein the user interface is furthermore adapted for displaying an overview comprising a representation regarding each of the plurality of monitors at their relative position and the imaging data displayed on the respective monitors.

10. An audiovisual controller according to claim 8, wherein the representation regarding each of the plurality of monitors at their relative position in the overview and an image displayed on different monitors is shown with a common visual element.

11. An audiovisual controller according to claim 10, wherein the common visual element is an indication in the same colour.

12. An audiovisual controller according to claim 10, wherein the controller is configured to, upon selection of a monitor of the plurality of monitors in the overview by a user, identify the monitor by an indication on that monitor.

13. An audiovisual controller according to claim 8, wherein the controller is configured to, upon activating a new monitor in the network, add the new monitor the overview.

14. An operating theater comprising an audiovisual controller according to claim 1.

* * * * *